United States Patent [19]
Coleman

[11] Patent Number: 5,807,105
[45] Date of Patent: *Sep. 15, 1998

[54] RATE CONTROLLED FLUID DELIVERY IN DENTAL APPLICATIONS

[76] Inventor: Thomas A. Coleman, P.O. Box 230, Shaftsbury, Vt. 05262

[ * ] Notice: The term of this patent shall not extend beyond the expiration date of Pat. No. 5,547,347.

[21] Appl. No.: 667,986

[22] Filed: Jun. 19, 1996

Related U.S. Application Data

[63] Continuation-in-part of Ser. No. 327,378, Oct. 21, 1994, Pat. No. 5,547,374.

[51] Int. Cl.⁶ ................................................. A61C 1/12
[52] U.S. Cl. ................................................ 433/85; 433/80
[58] Field of Search .................................. 433/80, 82, 84, 433/85, 89; 138/45, 46; 251/205, 206, 207, 208

[56] References Cited

U.S. PATENT DOCUMENTS

| | | |
|---|---|---|
| 2,696,049 | 12/1954 | Black . |
| 2,909,197 | 10/1959 | Liley . |
| 2,994,344 | 8/1961 | Kerley . |
| 3,762,439 | 10/1973 | Heath . |
| 4,116,239 | 9/1978 | Ewen . |
| 4,248,589 | 2/1981 | Lewis . |
| 4,249,899 | 2/1981 | Davis . |
| 4,655,246 | 4/1987 | Phlipot et al. . |
| 4,724,869 | 2/1988 | Carter . |
| 5,016,673 | 5/1991 | Carter et al. . |
| 5,150,880 | 9/1992 | Austin, Jr. et al. . |
| 5,275,561 | 1/1994 | Goldsmith . |
| 5,286,065 | 2/1994 | Austin et al. . |
| 5,332,194 | 7/1994 | Austin, Jr. et al. . |

FOREIGN PATENT DOCUMENTS

| | | | |
|---|---|---|---|
| 3708736 | 10/1988 | Germany | .................................. 433/80 |

OTHER PUBLICATIONS

Parker, Dental Clinics of North America, 37:341–351, 1993.
Kerstein, Dentistry Today, 11:52–59, 1992.
Grippo, Journal of Esthetic Dentistry, 3:14–19, 1991.
Lee, et al., Prosthetic Dentistry, 52:374–380, 1984.
Sharav, et al., Archs Oral Biol., 27:305–310, 1982.
McCoy, Journal of Oral Implantology, 10:361–362, 1982.
Brady et al; JADA 94:726–729, 1977.
Bram et al; The Journal of Prosthetic Dentistry 67:718–722, 1992.
Chapman et al; The International Journal of Prosthdontics 4:377–381, 1991.
Goel et al; The Journal of Prosthetic Dentistry 66:451–459, 1991.
Kinney et al; JADA 123:49–54, 1992.
Laurell et al; The Journal of Prosthetic Dentistry 58:626–632, 1987.
Miskin; Florida Dental Journal 54:7–10, 1983.
Pashley; Focus On Adult Oral Health 1:1–5, 1993.
Rivera–Morales et al; The Journal of Prosthetic Dentistry 65:547–553, 1991.
Swenson; Journal/Indiana Dental Association 69:7–8, 1990.
Taylor et al; Journal of Prosthetic Dentistry 54:140–143, 1985.
Williamson et al; Journal of Prosthetic Dentistry 49:816–818, 1983.
Xhonga; Journal of Oral Rehabilitation 4:65–76, 1977.
Xhonga et al.; JADA 84:577–582, 1972.

*Primary Examiner*—Ren Yan
*Attorney, Agent, or Firm*—Fish & Richardson P.C.

[57] ABSTRACT

The improvement of a dental syringe includes the addition of a fluid control block. The fluid control block includes a barrel portion having a first connector for attachment to a syringe handle and a second connector for attachment to a delivery nozzle. The barrel portion defines an air flow passage and a separate water flow passage. A dial is rotatably mounted to the barrel portion and defines a plurality of differently sized flow orifices alignable one-at-a-time with one of the flow passages. Each of the flow orifices allows a predetermined level of fluid flow through the flow passage when aligned with the flow passage. The improved dental syringe can be employed to assess abfraction forces acting upon teeth, to assess the success or failure of an occlusal adjustment procedure, and to reduce splatter.

19 Claims, 3 Drawing Sheets

RATE CONTROLLED FLUID DELIVERY IN DENTAL APPLICATIONS

This application is a continuation-in-part of application Ser. No. 08/327,378, filed Oct. 21, 1994 now U.S. Pat. No. 5,547,374.

BACKGROUND OF THE INVENTION

The invention relates to rate controlled fluid delivery in dental applications.

A dental syringe delivering pressurized fluid to a wand tip has been described in U.S. Pat. No. 4,249,899. Such syringes are typically used to deliver a spray of water and/or air to a specific location in a patient's mouth.

SUMMARY OF THE INVENTION

In dental procedures, it is often desirable to deliver a controlled volume of fluid through a wand tip, e.g., when training dental professionals. Additionally, the inventor has determined that abfraction forces acting upon a tooth result in air sensitivity of respective teeth in the abfracted region; by providing controlled fluid release, abfraction forces acting upon a tooth can be identified and quantified, and a success or failure index provided for occlusal adjustment of hyperoccluded teeth.

It is therefore an object of the current invention to provide a flow control means which allows graded evaluation of air sensitivity of teeth at the cemento-enamel junction for intent of bite correction to reduce abfraction forces.

It is another object of the present invention to provide a teaching tool for training of dental health professionals in the use of air/water syringes. The reduction to the volume allows the novice operator to reduce flows and thereby limit unwanted splatter in clinical performance of dental procedures.

It is another object of the present invention to offer a range of graded capabilities for standard air/water syringe emissions of air and/or water.

In one embodiment of the present invention, the improvement of a dental syringe comprising an air source and a water source includes the addition of a fluid control block. The fluid control block includes a barrel portion having a first connector for attachment to a syringe handle and a second connector for attachment to a delivery nozzle. The barrel portion defines at least two separate passages, one of the passages being an air flow passage and the other of the passages being a water flow passage. A dial is rotatably mounted to the barrel portion and defines a plurality of differently sized flow orifices alignable one-at-a-time with one of the flow passages. Each of the flow orifices allows a predetermined level of fluid flow through the flow passage when aligned with the flow passage.

Preferred embodiments of the invention may include one or more of the following aspects. The dial is configured for alignment of the flow orifices with the air flow passage. The barrel portion defines a slot in which the dial is rotatably mounted to the barrel portion. A pivot pin is included for rotatably mounting the dial to the barrel portion. The dial defines a centrally located pivot hole for placement of the pivot pin therethrough and the barrel portion defines a centrally offset pivot hole wherein an end of the pivot pin is connected.

The flow orifices are radially spaced about the centrally located pivot hole, the flow orifices being alignable with the air flow passage by rotation of the dial about the pivot pin.

A detent pin is included for preventing rotation of the dial about the pivot pin. The barrel portion defines a detent hole for placement of the detent pin therein. The dial defines a plurality of detent pin indentations, an end of the detent pin is located in one of the detent pin indentations when one of the flow orifices is aligned with the air flow passage.

The detent hole is located radially the same distance as the centrally located flow passage from the pivot pin, and each of the detent pin indentations is coaxially located about one of the flow orifices, one of the flow orifices being aligned with the air flow passage when another of the flow orifices is aligned with the detent pin.

The dial includes a knurled edge for finger rotation of the dial and placement markers located on the knurled edge indicate the position of the flow orifices with respect to the flow passage.

A deformable connecting member is positioned between the dial and the air flow passage. The connecting member is designed to vent excess air pressure in the air flow passage to atmosphere during operation of the syringe. The deformable connecting member is an o-ring located in the air flow passage on a first side of the dial between the barrel portion and the dial. A second o-ring is located on the side of the dial opposite the first side between the dial and the barrel portion. Venting of excess pressure to atmosphere occurs between the dial and the o-rings.

A deformable member separates the air flow passage and the water flow passage at an inlet end of the barrel portion.

The barrel portion is formed from two joinable sections. A deformable member seals the water flow passage upon joining of the two joinable sections.

The delivery nozzle is a wand tip.

In another aspect of the invention, a dental syringe assembly including a fluid control block having a barrel portion and a dial rotatably mounted to the barrel portion, includes a detent member positioned to exert force to maintain the dial in a position aligning one of the orifices of the dial with the flow passages. The force is sufficiently small that it can be overcome with the user's finger, allowing rotation of the dial to align a second orifice with the flow passage.

Another aspect of the invention generally features a method of indirectly assessing abfractive forces upon a tooth. In the method, a controlled volume of air is delivered to teeth. The sensitivity of a tooth to the delivered fluid is determined. The sensitivity is used to identify and quantify excessive forces acting upon the tooth.

Another aspect of the invention generally features a method of assessing the success or failure of an occlusal adjustment procedure. In the method, a controlled volume of air is delivered to teeth. The level of sensitivity of teeth to air is measured before an occlusal adjustment procedure. The level of sensitivity of teeth to air is measured after an occlusal adjustment procedure. The sensitivities measured before and after the occlusal adjustment procedure are compared with a decrease in sensitivity indicating an improved bite resulting from reduced abfractive forces.

Another aspect of the invention generally features a method of reducing splatter when using a dental syringe comprising an air source and a water source employing the fluid control block of the invention. In the method, the dial is rotated to align a desired flow orifice with the flow passage, the desired flow orifice providing fluid flow at a desired fluid pressure. The fluid flow is delivered to a patient's mouth.

Preferred embodiment of this aspect of the invention may include barrel portion defining at least two separate passages, one of the passages being an air flow passage and the other of the passages being a water flow passage, the method including rotating the dial to align a desired flow orifice with one of the flow passages. The dial is preferably aligned with the air flow passage.

Other features and advantages of the invention will be apparent from the following description of the preferred embodiment thereof, and from the claims.

DESCRIPTION OF THE PREFERRED EMBODIMENT

Figure 1:
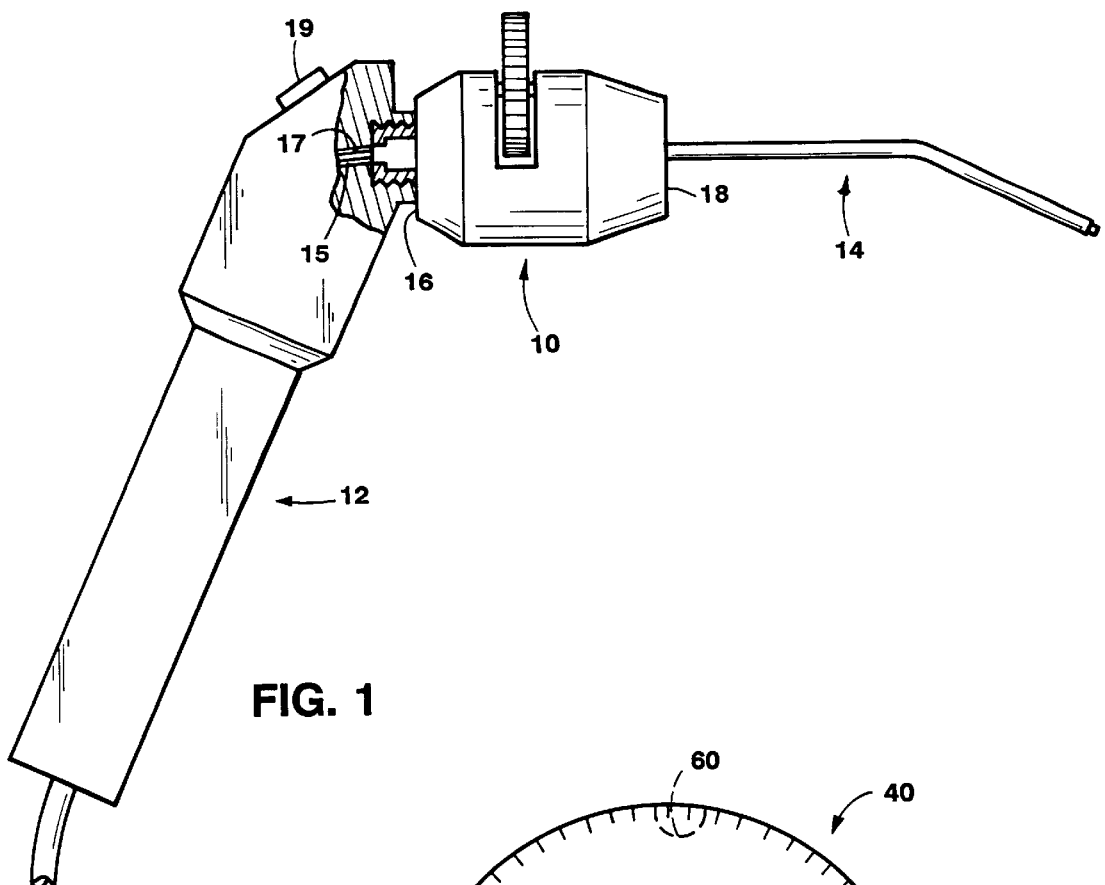
FIG. 1 is a diagrammatic representation of the fluid control block for controlled delivery of fluid from an air/water syringe to a wand tip.

Referring to FIG. 1, fluid control block 10 provides controlled delivery of fluid from a pressurized source, e.g., a standard dental air/water supply (not shown). Fluid control block 10 is attached at proximal end 16 to syringe handle 12 and at distal end 18 to a dental device, e.g., standard wand tip 14 currently in use in dentistry.

Syringe handle 12 includes an air conduit 15 and a water conduit 17. Valves (not shown) control the flow of air and water into fluid control block 10 (see Davis U.S. Pat. No. 4,249,899 and Lewis U.S. Pat. No. 4,248,589, hereby incorporated by reference).

Figure 2A:
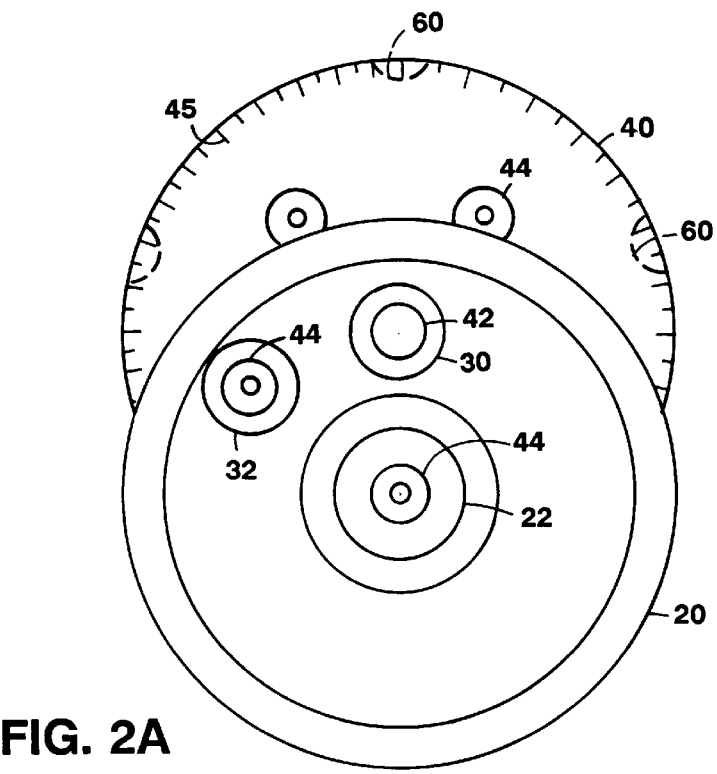
FIG. 2a is an end view of the fluid control block of FIG. 2 taken along the line 2a—2a, with the pivot pin and detent pin removed.
Figure 2:
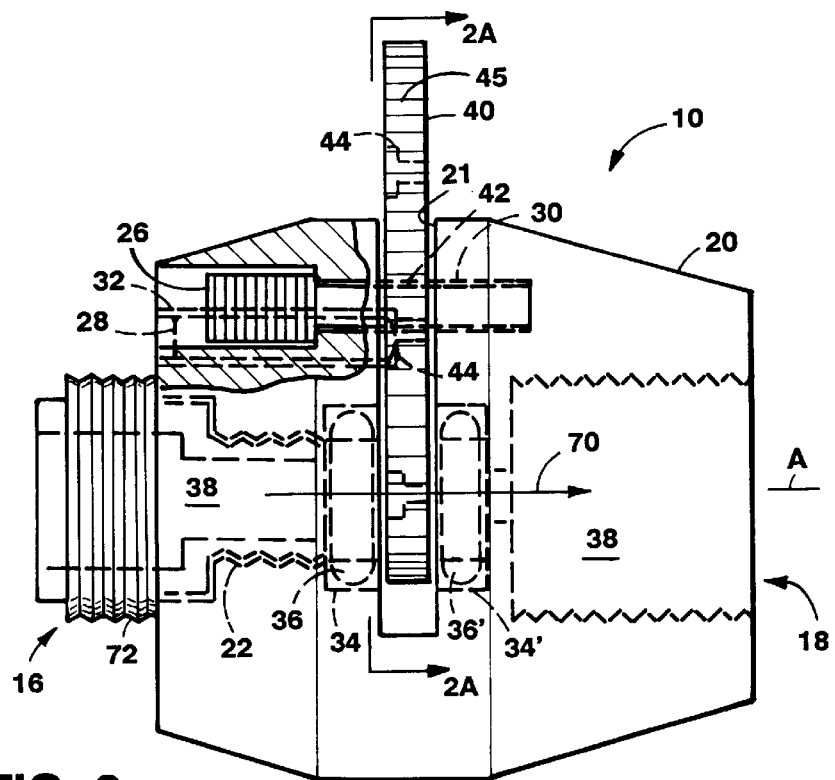
FIG. 2 is a partially cut away side view of the fluid control block.

Referring to FIGS. 2 and 2a, fluid control block 10 includes barrel portion 20 and dial 40 constructed of materials acceptable for dental use in accordance with standard disinfection and/or sterilization techniques, e.g., stainless steel, anodized aluminum, brass or other resilient material. Barrel portion 20 includes slot 21 having a width, e.g, of 0.062", in which dial 40 is located. Barrel portion 20 has a maximum diameter, e.g., of 0.62" and dial 40 has a diameter, e.g., of 0.604", and a thickness, e.g., of 0.06".

Fluid control block 10 defines a flow passage 38 aligned with an axis, A for fluid flow along arrow 70. A threaded hole 22 defined by barrel portion 20 at proximal end 16 accepts male connector 72 which connects fluid control block 10 to syringe 12. A second threaded hole 24 defined by barrel portion 20 at distal end 18 connects fluid control block 10 to wand tip 14.

Barrel portion 20 and dial 40 are rotatably connected via a pivot pin 26. Pivot pin 26 is passed through centrally located hole 42 in dial 40 and screwed into place in the threaded portion of a hole 30 defined by barrel portion 20. A detent pin e.g., spring loaded ball plunger 28, is positionable to prevent rotation of dial 40 about pivot pin 26. A hole 32 in barrel portion 20 and a plurality of detent indentations 44 in dial 40 receive plunger 28. Detent indentations 44 go partially through the thickness of dial 40, e.g., 0.04" deep.

Barrel portion 20 defines two O-ring recesses 34, 34' for receiving o-rings 36, 36'. O-rings 36, 36' are retained in position on one side by frictional force against dial 40 and on the other by recesses 34, 34'.

Figure 3:
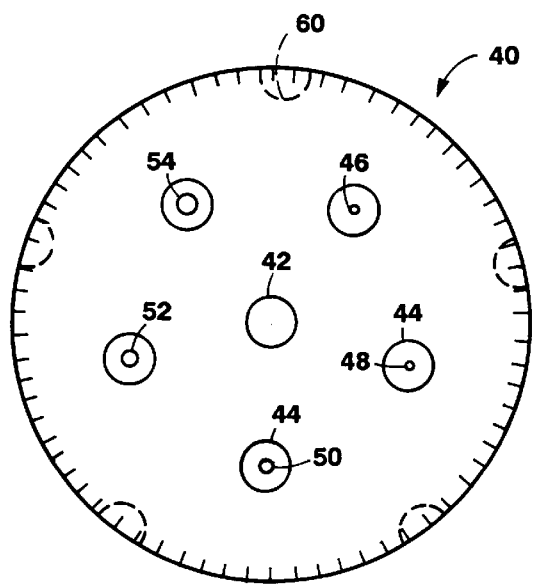
FIG. 3 shows the dial of the invention.

Referring also to FIG. 3, detent indentations 44 are concentrically located about a plurality of flow orifices 46, 48, 50, 52 and 54 of varying diameters, e.g., 0.005", 0.0075", 0.0102", 0.0135" and 0.045" respectively, equally spaced about the center of dial 40. The diameter of flow orifice 54 corresponds to the diameter of the syringe's flow passage to provide for a flow rate through fluid control block 10 equal to that of the flow rate through the syringe.

The edge of dial 40 includes serrations 45 for ease of finger pressure rotation and includes machined indentations 60 which serve as indicators of the position of the flow orifices with respect to flow passage 38 to facilitate alignment of a desired flow orifice in the flow passage.

Incoming air pressure from a dental air/water supply is commonly 20–50 P.S.I. Due to the sizes of the flow orifices in dial 40, incoming air pressure is great enough that excess pressure generally vents around o-ring 36. Due to this release, air pressure released into wand tip 14 from fluid control block 10 is as little as 2–3 P.S.I. with the smallest orifice 46 in place, approximately 14–17 P.S.I. with the third largest orifice 50 in place, and increases with larger orifices, the air pressure released into wand tip 14 with the largest orifice 54 in place being that of the supply pressure.

Dial 40 may be easily disassembled by removal of pivot pin 26 to allow cleaning for replacement of o-rings 36, 36'.

In use, air and/or water enters flow passage 38 from syringe 12. The flow rate is set by rotating dial 40 to align the desired flow orifice with flow passage 38 as indicated by indentations 60.

Fluid control block 10, used in combination with air/water syringe 12 and wand tip 14, can be used to assess abfraction of teeth. It has been theorized (see Grippo, J. O., Abfractions: A new Classification of Hard Tissue Lesions of Teeth, Journal of Esthetic Dentistry 1991; 3(1): 14–19) that abfraction of dentinal root structure at the cemento-enamel junction of a tooth is caused by tensile, compressive and/or shearing forces acting upon tooth enamel at the occluding table. Abfraction results in crazing or cracking of root dentin/enamel from the exterior inward, toward the central pulpal components of affected teeth.

By delivering a controlled volume of air or air/water mixture to a tooth and determining the sensitivity of the tooth to the delivered fluid, abfraction forces acting upon the tooth can be identified and quantified. Additionally, the level of sensitivity as measured before and after an occlusal adjustment procedure provides a success or failure index for the procedure, for example, a decrease in sensitivity indicates an improved bite.

Fluid control block 10, used in combination with air/water syringe 12 and wand tip 14, can be used to reduce the splatter sometimes associated with using a dental syringe. This is particularly useful for training purposes and during procedures, e.g., surgical procedures, where reduced splatter results in greater safety for dental personnel.

In an alternative embodiment of fluid control block 10, the number and size of flow orifices may vary from that described above.

In an alternative embodiment, the means of attachment of fluid control block 10 to syringe 12 and wand tip 14 may be of varied configuration as needed to companion these devices.

Figure 4:
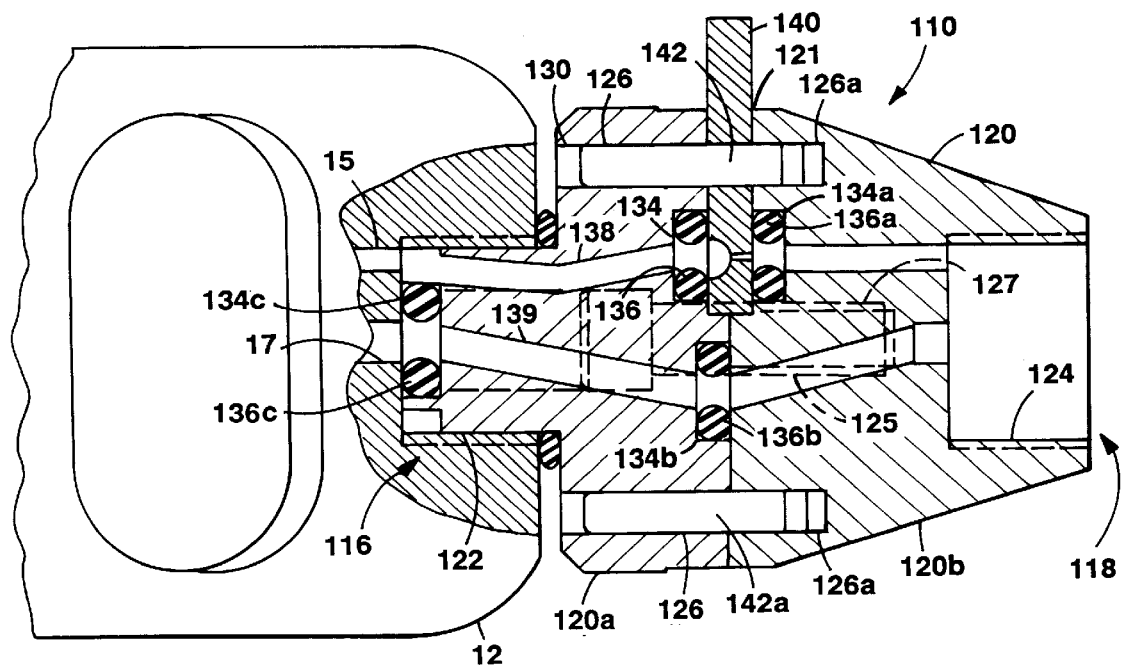
FIG. 4 is a cross-sectional view of an additional embodiment of a fluid control block.
Figure 5:
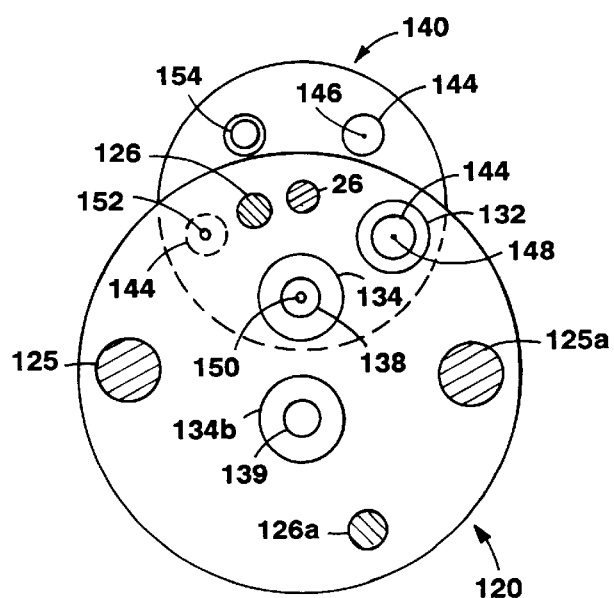
FIG. 5 is a view, similar to that of FIG. 2a, of the fluid control block of FIG. 4.

Referring to FIGS. 4 and 5, in another alternative embodiment, fluid control block 110 includes barrel portion 120 and dial 140. To ease machining of the barrel portion, barrel portion 120 is formed from first and second sections 120a, 120b connected by bolts 125, 125a. When connected, sections 120a, 120b define a slot 121 in which dial 140 is located.

Fluid control block 110 defines flow passages 138 and 139 for flow of air and water, respectively. A threaded portion 122 of barrel portion 120 at proximal end 116 connects fluid control block 110 to syringe 12. A threaded hole 124 defined by barrel portion 120 at distal end 118 connects fluid control block 110 to wand tip 14.

The two barrel portions 120a and 120b include recesses 126 and 126a for receiving friction fit pins 142 and 142a which position barrel portions 120a and 120b prior to tightening of bolts 125 and 125a into respective threaded orifices (threaded orifice 127 receiving bolt 125 being shown in FIG. 4). Barrel portion 120 further includes a detent pin and a pivot pin (not shown) which interact with dial 140 as described previously with reference to dial 40 of FIG. 2. Friction fit pins 142 and 142a and bolts 125 and 125a are located so as not to interfere with pivot pin 26 and detent pin 28.

Barrel portion 120 defines four O-ring recesses 134, 134a, 134b, 134c for receiving O-rings 136, 136a, 136b, 136c, respectively. O-rings 136 and 136a are retained in position on one side by frictional force against dial 140 and on the other by recesses 134, 134a. O-ring 136b provides a seal between barrel portion sections 120a and 120b along water passage 139. O-ring 136c acts to seal off water passage 139 from air passage 138 at the inlet end (proximal end 116).

As in the embodiment of FIG. 2, detent indentations 144 are concentrically located about a plurality of flow orifices 146, 148, 150, 152 and 154 of varying diameters. The edge of dial 140 may be serrated for ease of finger pressure rotation and include indicators of the position of the flow orifices with respect to air passage 138 to facilitate alignment of a desired flow orifice in the air passage. Incoming air pressure from a dental air/water supply is commonly 20–50 P.S.I. Due to the sizes of the flow orifices in dial 140, incoming air pressure is great enough that excess pressure generally vents around O-ring 136.

The separate passages 138 and 139 of the fluid control block 110 of FIGS. 4 and 5, helps avoid any unwanted mixing of water in with air when it is desired to deliver only air to wand tip 14 following the delivery of a mixture of air and water to the wand tip.

Other embodiments are within the following claims.

For example, fluid control block 110 may be configured such that the flow orifices of dial 140 are alignable with water flow passage 139. One or two dials may be configured to align flow orifices with both the air and water flow passages.

What is claimed is:

1. A dental syringe assembly for attachment to an air source and a water source, the assembly comprising a fluid control block comprising:
    a) a barrel portion having a first connector for attachment to an air/water syringe and a second connector for attachment to a delivery nozzle, said barrel portion defining at least two separate passages, one of the passages being an air flow passage and the other of the passages being a water flow passage,
    b) a dial rotatably mounted to said barrel portion, said dial defining a plurality of differently sized flow orifices alignable one-at-a-time with one of said flow passages, each of said flow orifices allowing a predetermined level of fluid flow through said one of said flow passages when aligned with said one of said flow passages, and
    c) a deformable connecting member positioned between said dial and said flow passage, said connecting member being designed to vent excess air pressure in said flow passage to atmosphere during operation of said syringe.

2. The dental syringe assembly of claim 1 wherein said dial is configured for alignment of said flow orifices with said air flow passage.

3. The dental syringe assembly of claim 1 wherein said barrel portion further defines a slot in which said dial is rotatably mounted to said barrel portion.

4. The dental syringe assembly of claim 3 including a pivot pin for rotatably mounting said dial to said barrel portion, said dial defining a centrally located pivot hole for placement of said pivot pin therethrough and said barrel portion defining a centrally offset pivot hole wherein an end of said pivot pin is connected.

5. The dental syringe assembly of claim 4 wherein said flow orifices are radially spaced about said centrally located pivot hole, said flow orifices being alignable with said air flow passage by rotation of said dial about said pivot pin.

6. The dental syringe assembly of claim 5 including a detent pin for preventing rotation of said dial about said pivot pin, said barrel portion defining a detent hole for placement of said detent pin therein, said dial defining a plurality of detent pin indentations, an end of said detent pin being located in one of said detent pin indentations when one of said flow orifices is aligned with said air flow passage.

7. The dental syringe assembly of claim 1 wherein said dial further includes a knurled edge for finger rotation of said dial.

8. The dental syringe assembly of claim 1 wherein said dial further includes placement markers for indicating the position of said flow orifices with respect to said flow passage.

9. The dental syringe assembly of claim 1 in which the deformable connecting member is an o-ring located in said air flow passage on a first side of said dial between said barrel portion and said dial, venting of excess pressure to atmosphere occurring around said o-ring.

10. The dental syringe assembly of claim 9 further comprising a second o-ring located on the side of said dial opposite said first side between said dial and said barrel portion, venting of excess pressure to atmosphere occurring around said second o-ring.

11. The dental syringe assembly of claim 1 further including a deformable member separating said air flow passage and said water flow passage at an inlet end of said barrel portion.

12. The dental syringe assembly of claim 1 wherein said barrel portion comprises two joinable sections.

13. The dental syringe assembly of claim 12 further including a deformable member for sealing said water flow passage upon joining of said two joinable sections.

14. The dental syringe assembly of claim 1 wherein the delivery nozzle is a wand tip.

15. The dental syringe assembly of claim 1 in which the dial can be rotated by finger pressure.

16. A method of using a dental syringe assembly to deliver air and water to a patient, said method including the steps of:
    providing a fluid control block including a barrel portion having a first connector for attachment to a syringe handle and a second connector for attachment to a delivery nozzle, said barrel portion defining a flow passage, a dial rotatably mounted to said barrel portion, said dial defining a plurality of differently sized flow orifices alignable one-at-a-time with said flow passage, each of said flow orifices allowing a predetermined level of fluid flow through said flow passage when aligned with said flow passage, and a deformable connecting member positioned between said dial and said flow passage, said connecting member being designed to vent excess air pressure in said flow passage to atmosphere during operation of said syringe, attaching the assembly to an air source at between 20 and 50 psi;

rotating said dial to align a desired flow orifice with said flow passage, said desired flow orifice providing fluid flow at a desired fluid pressure, delivering the fluid flow to a patient's mouth, whereby controlled fluid flow reduces splattering.

17. The method of claim 16, wherein said barrel portion defines at least two separate passages, one of the passages being an air flow passage and the other of the passages being a water flow passage, said flow orifices of said dial being alignable one-at-a-time with one of said flow passages, said method including rotating said dial to align a desired flow orifice with one of said flow passages.

18. The method of claim 17 wherein said dial is aligned with said air flow passage.

19. A dental syringe assembly for attachment to an air source and a water source, the assembly comprising a fluid control block comprising:

a) a barrel portion having a first connector for attachment to an air water syringe and a second connector for attachment to a delivery nozzle, said barrel portion defining at least two separate passages, one of the passages being an air flow passage and the other of the passages being a water flow passage, b) a dial rotatably mounted to said barrel portion, said dial defining a plurality of differently sized flow orifices alignable one-at-a-time with one of said flow passages, each of said flow orifices allowing a predetermined level of fluid flow through said one of said flow passages when aligned with said one of said flow passages, c) said barrel portion further defining a slot in which said dial is rotatably mounted to said barrel portion, d) a pivot pin for rotatably mounting said dial to said barrel portion, said dial defining a centrally located pivot hole for placement of said pivot pin therethrough and said barrel portion defining a centrally offset pivot hole wherein an end of said pivot pin is connected, said one of said flow passages being centrally located in said barrel portion, said flow orifices being radially spaced about said centrally located pivot hole and said flow orifices being alignable with said one of said flow passages by rotation of said dial about said pivot pin, and e) a detente pin for restricting rotation of said dial about said pivot pin, said barrel portion defining a detent hole for placement of said detent pin therein, said dial defining a plurality of detent pin indentations, an end of said detent pin being located in one of said detent pin indentations when one of said flow orifices is aligned with said one of said flow passages, said detent hole being located radially the same distance as the centrally located flow passage from said pivot pin, and each of said detent pin indentations being coaxially located about one of said flow orifices, one of said flow orifices being aligned with said one of said flow passages when another of said flow orifices is aligned with said detent pin.

* * * * *